US012691116B2

(12) United States Patent
Du et al.

(10) Patent No.: US 12,691,116 B2
(45) Date of Patent: Jul. 28, 2026

(54) SETBP1 AND XPO1 INHIBITORS FOR THE TREATMENT OF SICKLE CELL DISEASE AND β-THALASSEMIA

(71) Applicant: The Henry M. Jackson Foundation for the Advancement of Military Medicine, Inc., Bethesda, MD (US)

(72) Inventors: Yang Du, Gaithersburg, MD (US); Nhu Nguyen, Rockville, MD (US); Kristbjorn Gudmundsson, Silver Spring, MD (US)

(73) Assignee: The Henry M. Jackson Foundation for the Advancement of Military Medicine, Inc., Bethesda, MD (US)

( * ) Notice: Subject to any disclaimer, the term of this patent is extended or adjusted under 35 U.S.C. 154(b) by 1192 days.

(21) Appl. No.: 17/616,158

(22) PCT Filed: Jun. 4, 2020

(86) PCT No.: PCT/US2020/036151
§ 371 (c)(1),
(2) Date: Dec. 2, 2021

(87) PCT Pub. No.: WO2020/247654
PCT Pub. Date: Dec. 10, 2020

(65) Prior Publication Data
US 2022/0249486 A1 Aug. 11, 2022

Related U.S. Application Data

(60) Provisional application No. 62/858,103, filed on Jun. 6, 2019.

(51) Int. Cl.

| | |
|---|---|
| ***A61K 31/517*** | (2006.01) |
| ***A61K 31/4745*** | (2006.01) |
| ***A61K 31/7088*** | (2006.01) |
| ***A61K 31/7105*** | (2006.01) |
| ***A61K 38/46*** | (2006.01) |
| ***A61P 7/06*** | (2006.01) |

(52) U.S. Cl.
CPC ........ *A61K 31/517* (2013.01); *A61K 31/4745* (2013.01); *A61K 31/7088* (2013.01); *A61K 31/7105* (2013.01); *A61K 38/465* (2013.01); *A61P 7/06* (2018.01)

(58) Field of Classification Search
CPC ...... A61K 31/517; A61K 31/4745; A61P 7/06
See application file for complete search history.

(56) References Cited

U.S. PATENT DOCUMENTS 4,310,667 A * 1/1982 Le Pecq ............... C07D 209/88 546/70
2016/0168594 A1 6/2016 Zhang et al.
2016/0237455 A1 8/2016 Glucksmann et al.
2017/0020847 A1 1/2017 Hermine et al.
2019/0167710 A1 6/2019 Tang et al.

FOREIGN PATENT DOCUMENTS

WO WO 2019/226773 11/2019

OTHER PUBLICATIONS

Eadon, M. T.; et al. "Genetic and epigenetic variants contributing to clofarabine cytotoxicity" 2013, Human Molecular Genetics, vol. 22, pp. 4007-4020. (Year: 2013).*
Auclair, C.; et al. "Physicochemical and Pharmacological Properties of the Antitumor Ellipticine Derivative 2-(Diethylamino-2-ethyl)9-hydroxy Ellipticinium-Chloride, HCl" 1987, Cancer Research, vol. 47, pp. 6254-6261. (Year: 1987).*
Chang, K.-H.; et al. "Malarial anaemia: mechanisms and implications of insufficient erythropoiesis during blood-stage malaria" 2004, International Journal of Parasitology, vol. 34, pp. 1501-1516. (Year: 2004).*
Hohl, R.; et al. "Apparatus for measuring rat body volume: a methodological proposition" 2007, Journal of Applied Physiology, vol. 102, pp. 1229-1234. (Year: 2007).*
Pallardy, M.; et al. "Antibody recognition of substituted ammonium ions: Modulation by the counterion" 1987, Journal of Immunological Methods, vol. 99, pp. 179-183. (Year: 1987).*
Probst, R. J.; et al. "Gender Differences in the Blood Volume of Conscious Sprague-Dawley Rats" 2006, Journal of the American Association for Laboratory Animal Science, vol. 45, pp. 49-52. (Year: 2006).*
Kadia, T. M.; et al. "New Drugs in Acute Myeloid Leukemia", Annals of Oncology 2016, vol. 27, pp. 770-778. (Year: 2016).*
Mayani, H.; et al. "Biology of Human Hematopoietic Stem and Progenitor Cells Present in Circulation" Archives of Medical Research 2003, vol. 34, pp. 476-488. (Year: 2003).*
Wasmuth, C. E.; et al. "Blood Volume Determinations in the Operative Period", Cleveland Clinic Quarterly, 1955, vol. 22, pp. 124-130; cited in PTO-892. (Year: 1955).*
Han, W.; et al. "Base editing of the HBG promoter induces potent fetal hemoglobin expression with no detectable offtarget mutations in human HSCs" Cell Stem Cell 2023, vol. 30, pp. 1624-1639. (Year: 2023).*

(Continued)

*Primary Examiner* — Andrea Olson
*Assistant Examiner* — Benjamin M Brandsen
(74) *Attorney, Agent, or Firm* — Sheppard Mullin Richter & Hampton LLP

(57) ABSTRACT

The present disclosure relates to compounds that inhibit SETBP1 or XP01 activities. Also disclosed are methods of using such compounds to increase the expression of embryonic and fetal hemoglobin molecules, and to treat sickle cell disease and β-thalassemia. The present invention relates to unexpected findings that transcription factor SETBP1 regulates embryonic and fetal hemoglobin repression, and inhibition of SETBP1 can induce the expression of embryonic and fetal hemoglobins.

7 Claims, 8 Drawing Sheets

Specification includes a Sequence Listing.

(56) References Cited

OTHER PUBLICATIONS

Ranganathan, P.; et al. "Preclinical activity of a novel CRM1 inhibitor in acute myeloid leukemia", Blood 2012, vol. 120, pp. 1765-1773. (Year: 2012).*

International Search Report & Written Opinion dated Sep. 28, 2020 for PCT/US2020/036151. 19 pages.

* cited by examiner

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic

<400> SEQUENCE: 1

cggctttgaa tcccaatcat t                                              21


<210> SEQ ID NO 2
<211> LENGTH: 21
<212> TYPE: DNA
<213> ORGANISM: Artificial Sequence
```

-continued

<220> FEATURE:
<223> OTHER INFORMATION: Synthetic

<400> SEQUENCE: 2
cctatgatga accttggtta t 21

SETBP1 AND XPO1 INHIBITORS FOR THE TREATMENT OF SICKLE CELL DISEASE AND β-THALASSEMIA

CROSS-REFERENCE TO RELATED APPLICATIONS

This application is a U.S. National Stage Application under 35 U.S.C. § 371 of International Application No. PCT/US2020/036151, filed Jun. 4, 2020, which claims priority to U.S. Provisional Application No. 62/858,103, filed Jun. 6, 2019, which is incorporated herein by reference for all purposes.

STATEMENT REGARDING FEDERALLY SPONSORED RESEARCH OR DEVELOPMENT

This disclosure was made with government support under grant numbers HU00011920059 and PED-86-4142 awarded by the Uniformed Services University of the Health Sciences (USUHS). The government has certain rights in the invention.

SEQUENCE LISTING

The instant application contains a Sequence Listing which has been submitted in ASCII format via EFS-Web and is hereby incorporated by reference in its entirety. Said ASCII copy, created on Jun. 4, 2020, is named 316990_ST25.txt and is 702 bytes in size.

FIELD

The present disclosure relates to compounds and methods of inhibiting SETBP1 and XPO1 activities, enhancing the expression levels of embryonic and fetal hemoglobin molecules, and treating sickle cell disease and β-thalassemia.

BACKGROUND

β-globinopathies include sickle cell disease (SCD) and β-thalassemia and are among the most common monogenic disorders worldwide. SCD results from the synthesis of an abnormal hemoglobin, which tends to aggregate under low oxygen conditions while β-thalassemia results from the reduced expression or absence of β-globins (Bauer et al., Blood 120(15): 2945-53 (2012)). Large numbers of children are born worldwide with β-globinopathies each year, with approximately 300,000 having SCD and 40,000 having β-thalassemia (Weatherall, Blood 115(22): 4331-6 (2010)).

Treatment and management of SCD is mostly focused on pain relief and blood transfusions (Yawn et al., JAMA 312(10): 1033-48 (2014)). In β-thalassemia, blood transfusions are often needed throughout the patient's life (Olivieri et al., Cold Spring Harb. Perspect. Med. 3(6) (2013)). However, repeated blood transfusions can lead to iron overload, which is a major complication affecting both cardiovascular and liver functions. As a result, other therapeutic options are being actively explored, including bone marrow transplantation and treatments to reactivate the expression of embryonic and fetal hemoglobins (Bauer et al., Blood 120(15): 2945-53 (2012)). Bone marrow transplantation is currently the only curative treatment available for SCD in adults (Hsieh et al., N. Engl. J. Med. 361(24): 2309-17 (2009); Hsieh et al., JAMA 312(1): 48-56 (2014)).

However, both the high cost associated with this procedure and the difficulty in finding matched donors have prevented its broad usage.

Fetal hemoglobin (HbF) expression can be induced by non-targeted drug treatments such as hydroxyurea (Esrick et al., Am. J. Hematol. 90(7): 624-8 (2015); Wong et al., Blood 124(26): 3850-7 (2014)). However, the induction efficiency by hydroxyurea is low and treatment is not effective for all patients. Effective small molecules for inducing embryonic and fetal hemoglobin expression, and thereby treating SCD and β-thalassemia, remain to be identified.

SUMMARY

The present invention relates to unexpected findings that transcription factor SETBP1 regulates embryonic and fetal hemoglobin repression, and inhibition of SETBP1 can induce the expression of embryonic and fetal hemoglobins.

In some embodiments, the present invention is directed to small molecule compounds that inhibit SETBP1 or XPO1 activities, and the use of these compounds in inducing the expression levels of embryonic and fetal hemoglobins that can be used as effective therapeutics for sickle cell disease and β-thalassemia.

Provided herein are methods for treating sickle cell disease in a subject in need thereof, comprising administering to the subject a therapeutically effective amount of a SETBP1 inhibitor, an XPO1 inhibitor, or a combination of a SETBP1 inhibitor and an XPO1 inhibitor.

Also provided herein are methods for treating β-thalassemia in a subject, comprising administering to the subject a therapeutically effective amount of a SETBP1 inhibitor or a combination of a SETBP1 inhibitor and an XPO1 inhibitor.

Also provided herein are methods of inducing embryonic and fetal hemoglobin expression in a cell, wherein the cell is a hematopoietic progenitor cell, an erythroid progenitor cell, or an erythroid cell, comprising contacting the cell with a SETBP1 inhibitor, an XPO1 inhibitor, or a combination of a SETBP1 inhibitor and an XPO1 inhibitor.

BRIEF DESCRIPTION OF THE DRAWINGS

The following figures are merely illustrative of specific embodiments of the invention and are not intended to otherwise limit the full scope of the invention as described.

(FIG. 8D) Representative bar graphs showing mRNA levels of human embryonic and fetal hemoglobin (γ+ε) as a percentage of total β-like globin (β+γ+ε) mRNA levels after treatment with Compound 1AA and 1BB versus DMSO. Note that a level of 20% or above for embryonic and fetal hemoglobin is considered curative for sickle cell disease. , $P<0.01$; *, $P<0.001$; ****$P<0.0001$ (two-tailed Student's t test).

DETAILED DESCRIPTION

Definitions

Figure 1:
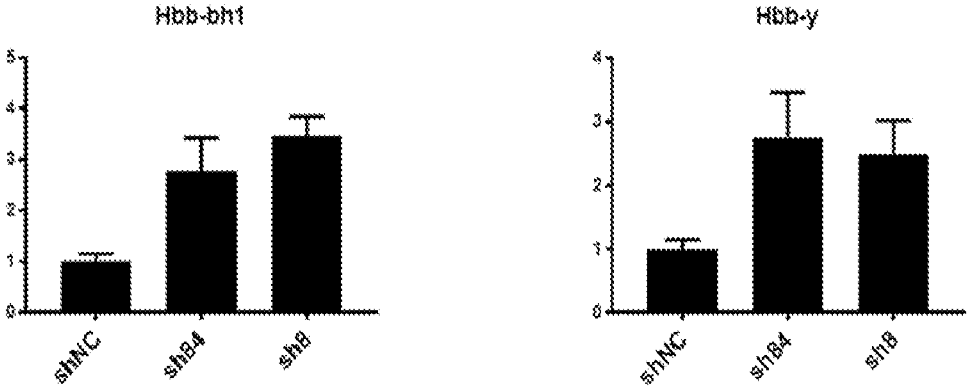
FIG. 1 shows that Setbp1 knockdown increased embryonic and fetal hemoglobin expression levels in MEL cells. Real-time RT-PCR analysis of Hbb-bh1 and Hbb-y mRNA levels in MEL cells at 72 hours after infection with lentiviral shRNAs targeting Setbp1 (sh84 and sh8) or non-targeting control lentiviral shRNA (shNC). Relative expression levels were calculated by normalizing to Rpl4 mRNA levels in the same sample and also to cells infected with shNC virus.

The term "alkyl," as used herein, means any straight chain or branched, non-cyclic or cyclic, unsaturated or saturated aliphatic hydrocarbon containing, for example, from 1 to 20 carbon atoms, while the term "lower alkyl" has the same meaning as alkyl but contains from 1 to 5 carbon atoms. The term "higher alkyl" has the same meaning as alkyl but contains from 6 to 20 carbon atoms. Representative saturated straight chain alkyls include, but are not limited to, methyl, ethyl, n-propyl, n-butyl, n-pentyl, n-hexyl, n-heptyl, n-octyl, n-nonyl, and the like; while saturated branched alkyls include, but are not limited to, isopropyl, sec-butyl, isobutyl, tert-butyl, isopentyl, and the like. Cyclic alkyls may be obtained by joining two alkyl groups bound to the same atom or by joining two alkyl groups each bound to adjoining atoms. Representative saturated cyclic alkyls include, but are not limited to, cyclopropyl, cyclobutyl, cyclopentyl, cyclohexyl, and the like; while unsaturated cyclic alkyls include, but are not limited to, cyclopentenyl and cyclohexenyl, and the like. Cyclic alkyls are also referred to herein as "cycloalkyls," "homocycles" or "homocyclic rings." Unsaturated alkyls contain at least one double or triple bond between adjacent carbon atoms (referred to as an "alkenyl" or "alkynyl," respectively). Representative straight chain and branched alkenyls include, but are not limited to, ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include, but are not limited to, acetylenyl, propynyl, 1-butynyl, 2-butynyl, 1-pentynyl, 2-pentynyl, 3-methyl-1-butynyl, and the like.

The term "aryl," as used herein, refers to any aromatic carbocyclic moiety containing, for example, 5 to 20 carbon atoms such as, but not limited to, phenyl or naphthyl.

The term "arylalkyl," or "aralkyl" as used herein, refers to any alkyl having at least one alkyl hydrogen atom replaced with an aryl moiety, such as benzyl, but not limited to, $(CH_2)_2$phenyl, —$(CH_2)_3$phenyl, —CH(phenyl)$_2$, and the like.

The term "halogen" or "halo" as used herein, refers to any fluoro, chloro, bromo, or iodo moiety.

The term "haloalkyl" as used herein, refers to any alkyl having at least one hydrogen atom replaced with halogen, such as trifluoromethyl, and the like.

The term "heteroaryl" as used herein, refers to any aromatic heterocycle ring of 5 to 20 members and having at least one heteroatom selected from nitrogen, oxygen and sulfur, and containing at least one carbon atom, including, but not limited to, both mono- and bicyclic ring systems. Representative heteroaryls include, but are not limited to, furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, or quinazolinyl.

The term "heteroarylalkyl" as used herein, refers to any alkyl having at least one alkyl hydrogen atom replaced with a heteroaryl moiety, such as —CHpyridinyl, —$CH_2$pyrimidinyl, and the like.

The term "heterocycle" or "heterocyclic," "heterocyclyl" or "heterocyclic ring," as used herein, refers to any non-aromatic 3- to 7-membered monocyclic or any non-aromatic 7- to 10-membered bicyclic heterocyclic ring which is either saturated or unsaturated and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be attached via any heteroatom or carbon atom. Heterocycles may include, but are not limited to, morpholinyl, pyrrolidinonyl, pyrrolidinyl, piperidinyl, piperazinyl, imidazolinyl, imidazolidinyl, pyrazolinyl, pyrazolidinyl, 1,4-dioxanyl, dithianyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "heterocycloalkyl," as used herein, refers to any alkyl having at least one alkyl hydrogen atom replaced with a heterocycle, such as —$CH_2$morpholinyl, and the like.

The term "homocycle" or "cycloalkyl," as used herein, refers to any saturated or unsaturated (non-aromatic) carbocyclic ring containing from 3-7 carbon atoms, such as, but not limited to, cyclopropane, cyclobutane, cyclopentane, cyclohexane, cycloheptane, cyclohexene, and the like.

The term "alkylamino," as used herein, refers to at least one alkyl moiety attached through a nitrogen bridge (i.e., —N-(alkyl)N, such as a dialkylamino) including, but not limited to, methylamino, ethylamino, dimethylamino, diethylamino, and the like.

The term "alkyloxy" or "alkoxy", as used herein, refers to any alkyl moiety attached through an oxygen bridge (i.e., —O-alkyl) such as, but not limited to, methoxy, ethoxy, and the like.

The term "alkylthio." as used herein, refers to any alkyl moiety attached through a sulfur bridge (i.e., —S— alkyl) such as, but not limited to, methylthio, ethylthio, and the like.

The term "salts" as used herein, refers to any salt that complexes with identified compounds described herein. Examples of such salts include, but are not limited to, acid addition salts formed with inorganic acids (e.g., hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Salt compounds can also be administered as pharmaceutically acceptable quaternary salts known to a person skilled in the art, which specifically includes the quaternary ammonium salts of the formula —NRR'R"+Z—, wherein R, R', R" is independently hydrogen, alkyl, or benzyl, and Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate). Salt compounds can also be administered as pharmaceutically acceptable pyridine cation salts having a substituted or unsubstituted partial formula: wherein Z is a counter ion, including, but not limited to, chloride, bromide, iodide, alkoxide, toluenesulfonate, methylsulfonate, sulfonate, phosphate, or carboxylate (such as benzoate, succinate, acetate, glycolate, maleate, malate, fumarate, citrate, tartrate, ascorbate, cinnamoate, mandeloate, and diphenylacetate).

The term, "pharmaceutically acceptable carrier" as used herein, includes any and all solvents, or a dispersion medium including, but not limited to, water, ethanol, a polyol (for example, glycerol, propylene glycol, and liquid polyethylene glycol, and the like), suitable mixtures thereof, and vegetable oils, coatings, isotonic and absorption delaying agents, liposomes, commercially available cleansers, and the like. Supplementary bioactive ingredients also can be incorporated into such carriers.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In various exemplary embodiments, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "induce", "inducing", "induction" and grammatical equivalents when in reference to the expression of genes or proteins in a treated subject or a treated cell relative to a untreated subject or a untreated cell, mean that the quantity and/or levels of the genes or proteins in the treated subject or treated cell is greater than that in the untreated subject or untreated cell by any amount that is recognized as clinically relevant by any medically trained personnel. In various exemplary embodiments, the quantity and/or levels of the genes or proteins in the treated subject or treated cell is at least 10% greater than, at least 25% greater than, at least 50% greater than, at least 75% greater than, and/or at least 90% greater than the quantity and/or levels of the genes or proteins in the untreated subject or untreated cell.

The term "inhibitory compound" as used herein, refers to any compound capable of interacting with (i.e., for example, attaching, binding etc.) to a binding partner under conditions such that the binding partner becomes unresponsive to its natural ligands. Inhibitory compounds may include, but are not limited to, small organic molecules, antibodies, and proteins/peptides.

The term "attached" as used herein, refers to any interaction between a medium (or carrier) and a drug. Attachment may be reversible or irreversible. Such attachment includes, but is not limited to, covalent bonding, ionic bonding, Van der Waals forces or friction, and the like. A drug is attached to a medium (or carrier) if it is impregnated, incorporated, coated, in suspension with, in solution with, mixed with, etc.

The term "drug" or "compound" as used herein, refers to any pharmacologically active substance capable of being administered which achieves a desired effect. Drugs or compounds can be synthetic or naturally occurring, non-peptide, proteins or peptides, oligonucleotides or nucleotides, polysaccharides or sugars.

The term "administered" or "administering," as used herein, refers to any method of providing a composition to a patient such that the composition has its intended effect on the patient. An exemplary method of administering is by a direct mechanism such as, local tissue administration (i.e., for example, extravascular placement), oral ingestion, transdermal patch, topical, inhalation, suppository, etc.

The term "patient," as used herein, is an animal, such as, for example, a mammal, such as, for example, a human that need not be hospitalized. For example, out-patients and persons in nursing homes are "patients." A patient may comprise any age of a human or non-human animal and therefore includes both adult and juveniles (i.e., children). It is not intended that the term "patient" connote a need for medical treatment, therefore, a patient may voluntarily or involuntarily be part of experimentation whether clinical or in support of basic science studies.

The term "subject" as used herein refers to a vertebrate, preferably a mammal, more preferably a primate, still more preferably a human. Mammals include, without limitation, humans, primates, wild animals, feral animals, farm animals, sports animals and pets. The subject may be a juvenile or an adult.

"Exportin 1" ("XPO1"), also known as chromosomal maintenance 1 (CRM1), is a protein that mediates the nuclear export of proteins and nucleic acids. In human, for instance, a representative sequence of the XPO1 protein is UniProt: O14980 (or RefSeq: NP_003391). The term "XPO1 inhibitor" refers to an agent that inhibits or reduces the expression or biological activity of XPO1. Example XPO1 inhibitors, whether antibodies, inhibitory nucleic acids, or small molecules, are well-known in the art. Specific XPO1 inhibitors are identified in, e.g., Q. Sun et al., Signal Transduct Target Ther. 1:16010 (2016); U.S. Pat. No. 9,861,615; and K. Parikh et al., J. of Hematol. & Oncol 7:78 (2014).

"SET binding protein 1" ("SETBP1") is a protein that binds SET and is a DNA-binding protein known to regulate gene transcription. In human, for instance, a representative sequence of the SETBP1 protein is UniProt: Q9Y6X0 (or RefSeq: NP_001123582, NP_056374, NP_001366070, or NP_001366071). The term "SETBP1 inhibitor" used herein refers to molecules that inhibit the activity of SETBP1 and/or inhibit the binding of SETBP1 to other proteins in a cell. Specific SETBP1 inhibitors, for example, are identified in WO2019/226773.

The term "therapeutically effective amount" or "effective amount" of a compound described herein or a pharmaceutically acceptable salt thereof means an amount sufficient to effect treatment when administered to a subject, to provide a therapeutic benefit such as amelioration of symptoms or slowing of disease progression. For example, a therapeutically effective amount may be an amount sufficient to decrease a symptom of a sickle cell disease. The therapeutically effective amount may vary depending on the subject, and disease or condition being treated, the weight and age of the subject, the severity of the disease or condition, and the manner of administering, which can readily be determined by one of ordinary skill in the art.

The instant inventors made the surprising and unexpected discovery, as the experimental examples demonstrated, that SETBP1 is a repressor of the transcription of the embryonic and fetal hemoglobin genes. In addition to the knock down experiments, small molecule SETBP1 inhibitors also demonstrated potent activation of embryonic and fetal hemoglobins.

In another surprising and unexpected finding, inhibition of XPO1 also led to significant activation of the embryonic and fetal hemoglobins, suggesting that XPO1 is a cofactor in the repression of embryonic and fetal hemoglobin transcription. These data therefore demonstrate that inhibition of SETBP1 and/or XPO1 can effectively treat diseases and conditions by increasing the production of embryonic and/or fetal hemoglobin.

An aspect of the invention is a method for treating a disease by activating the expression of embryonic hemoglobin in a subject, comprising administering to the subject a therapeutically effective amount of a SETBP1 inhibitor or an XPO1 inhibitor.

Another aspect of the invention is a method for treating a disease by activating expression of embryonic hemoglobin in a subject, comprising administering to a subject in need thereof a therapeutically effective amount of a SETBP1 inhibitor or a XPO1 inhibitor or a combination of a SETBP1 inhibitor and a XPO1 inhibitor.

Another aspect of the invention is a method for treating a disease by activating the expression of fetal hemoglobin in a subject, comprising administering to the subject a therapeutically effective amount of a SETBP1 inhibitor or an XPO1 inhibitor.

Another aspect of the invention is a method for treating a disease by activating expression of fetal hemoglobin in a subject, comprising administering to a subject in need thereof a therapeutically effective amount of a SETBP1 inhibitor or a XPO1 inhibitor or a combination of a SETBP1 inhibitor and a XPO1 inhibitor.

An exemplary embodiment of the invention is a method for treating sickle cell disease or β-thalassemia in a subject, comprising administering to the subject a therapeutically effective amount of a SETBP1 inhibitor.

Another exemplary embodiment of the invention is a method for treating sickle cell disease or D-thalassemia in a subject, comprising administering to the subject a therapeutically effective amount of an XPO1 inhibitor.

Another exemplary embodiment of the invention is a method for treating sickle cell disease or β-thalassemia in a subject, comprising administering to a subject in need thereof a therapeutically effective amount of a combination of a SETBP1 inhibitor and an XPO1 inhibitor.

Another exemplary embodiment of the invention is a method for treating sickle cell disease in a subject in need thereof, comprising administering to the subject a therapeutically effective amount of a SETBP1 inhibitor, an XPO1 inhibitor, or a combination of a SETBP1 inhibitor and an XPO1 inhibitor.

Another exemplary embodiment of the invention is a method for treating sickle cell disease (SCD) in a subject, comprising administering to a subject in need thereof a therapeutically effective amount of a SETBP1 inhibitor. Another exemplary embodiment of the invention is a method for treating sickle cell disease (SCD) in a subject, comprising administering to a subject in need thereof a therapeutically effective amount of a XPO1 inhibitor. Another exemplary embodiment of the invention is a method for treating sickle cell disease (SCD) in a subject, comprising administering to a subject in need thereof a therapeutically effective amount of a combination of a SETBP1 inhibitor and an XPO1 inhibitor.

In an exemplary embodiment, sickle cell disease is treated with a SETBP1 inhibitor.

In an exemplary embodiment, sickle cell disease is treated with an XPO1 inhibitor.

In an exemplary embodiment, sickle cell disease is treated with a combination of SETBP1 inhibitor and an XPO1 inhibitor.

In an exemplary embodiment, β-thalassemia is treated with a SETBP1 inhibitor.

In an exemplary embodiment, β-thalassemia is treated with an XPO1 inhibitor.

In an exemplary embodiment, β-thalassemia is treated with a combination of a SETBP1 inhibitor and an XPO1 inhibitor.

In an exemplary embodiment, the SETBP1 inhibitor is an shRNA or an siRNA. In an exemplary embodiment, the shRNA or the siRNA has a sequence that is at least 95% identical to the nucleic acid sequences selected from the group consisting of SEQ ID NO: 1 and SEQ ID NO: 2.

In an exemplary embodiment, the SETBP1 inhibitor is an anti-SETBP1 antibody inhibiting the activity of SETBP1 protein, a RNA molecule reducing SETBP1 transcription or translation, or a gene editing system disrupting the SETBP1 genomic sequence.

In an exemplary embodiment, the XPO1 inhibitor is an shRNA or an siRNA. In an exemplary embodiment, the XPO1 inhibitor is an anti-XPO1 antibody inhibiting the activity of XPO1 protein, a RNA molecule reducing SETBP1 transcription or translation, or a gene editing system disrupting the XPO1 genomic sequence.

In an exemplary embodiment, the SETBP1 inhibitor is a compound of Formula (1):

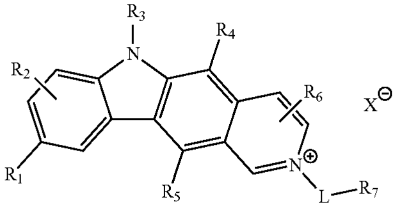

or a pharmaceutically acceptable salt thereof, wherein $R_1$ is —$OR_8$, —$SR_8$ or —$NR_8R_8$;

$R_2$, $R_3$, $R_4$, $R_5$ and $R_6$ are independently H or $C_{1-4}$ alkyl;

$R_7$ is —$NR_{10}R_{10}$ or a heterocyclyl group;

L is —$(CR_9R_9)_n$—;

X is an organic or inorganic anion;

each $R_8$ is independently H or $C_{1-3}$ alkyl;

each $R_9$ is independently H or $C_{1-3}$ alkyl;

each $R_{10}$ is independently H or $C_{1-3}$ alkyl; and n is 1, 2, 3 or 4.

In an exemplary embodiment of Formula (1), $R_1$ is —$OR_8$.

In an exemplary embodiment of Formula (1), $R_1$ is —$OR_8$ and $R_3$ is H.

In an exemplary embodiment of Formula (1), $R_1$ is —$OR_8$, $R_3$ is H, $R_8$ is H and each $R_9$ is H.

In an exemplary embodiment of Formula (1), n is 2.

In an exemplary embodiment of Formula (1), $R_1$ is —$OR_8$ and at least one $R_9$ is H.

In an exemplary embodiment of Formula (1), $R_1$ is —$NR_8R_8$, $R_3$ is H, each $R_8$ is H and each $R_9$ is H.

In an exemplary embodiment of Formula (1), at least one of $R_4$ and $R_5$ is —$CH_3$.

In an exemplary embodiment of Formula (1), each of $R_4$ and $R_5$ is —$CH_3$.

In an exemplary embodiment of Formula (1), $R_1$ is —$OR_8$, $R_2$ is H, $R_3$ is H and each of $R_4$ and $R_8$ is —$CH_3$.

In an exemplary embodiment of Formula (1), $R_7$ is a heterocyclyl group, where the heterocyclyl group is a 5- or 6-membered ring containing 1 or 2 nitrogen atoms.

In an exemplary embodiment of Formula (1), $R_7$ is a heterocyclyl group, $R_2$ is H and $R_1$ is —$OR_8$.

In an exemplary embodiment of Formula (1), $R_7$ is a heterocyclyl group, $R_2$ is H, $R_1$ is —$OR_8$ and $R_3$ is H.

In an exemplary embodiment of Formula (1), $R_7$ is a heterocyclyl group where the hetereocyclyl group is a piperidinyl group, $R_1$ is —$OR_8$, $R_2$ is H, $R_3$ is H, $R_8$ is H and each $R_9$ is H.

In an exemplary embodiment of Formula (1), $R_7$ is a heterocyclyl group where the hetereocyclyl group is a piperidinyl group, $R_2$ is H and at least one $R_9$ is H.

In an exemplary embodiment of Formula (1), $R_7$ is a heterocyclyl group where the hetereocyclyl group is a piperidinyl group, $R_2$ is H and each $R_9$ is H.

In an exemplary embodiment of Formula (1), $R_7$ is a heterocyclyl group where the hetereocyclyl group is a piperidinyl group, $R_2$ is H and at least one of $R_4$ and $R_8$ is —$CH_3$.

In an exemplary embodiment of Formula (1), $R_7$ is a heterocyclyl group where the hetereocyclyl group is a piperidinyl group, $R_2$ is H and each of $R_4$ and $R_5$ is —$CH_3$.

In an exemplary embodiment of Formula (1), $R_7$ is a heterocyclyl group where the hetereocyclyl group is a piperidinyl group, $R_1$ is —$OR_8$, $R_2$ is H, $R_3$ is H and each of $R_4$ and $R_5$ is —$CH_3$.

In an exemplary embodiment of Formula (1), X is F, Cl, Br or I.

In an exemplary embodiment of Formula (1), $R_1$ is a heterocyclyl group where the hetereocyclyl group is a piperidinyl group, $R_1$ is —$OR_8$, $R_2$ is H, $R_3$ is H, each of $R_4$ and $R_5$ is —$CH_3$ and X is F, Cl, Br or I.

In an exemplary embodiment of Formula (1), $R_7$ is —$NR_{10}R_{10}$.

In an exemplary embodiment of Formula (1), $R_7$ is —$NR_{10}R_{10}$ and each $R_{10}$ is independently $C_{1-3}$ alkyl.

In an exemplary embodiment of Formula (1), $R_7$ is —$NR_{10}R_{10}$ and one $R_{10}$ is $C_{1-3}$ alkyl and one $R_{10}$ is —H.

In an exemplary embodiment of Formula (1), $R_2$ is H, $R_7$ is —$NR_{10}R_{10}$ and each $R_{10}$ is —$CH_2CH_3$.

In an exemplary embodiment of Formula (1), $R_2$ is H, $R_7$ is —$NR_{10}R_{10}$ and each $R_{10}$ is H.

In an exemplary embodiment of Formula (1), $R_2$ is H, $R_7$ is —$NR_{10}R_{10}$, $R_1$ is —$OR_8$ and $R_3$ is H.

In an exemplary embodiment of Formula (1), $R_2$ is H, $R_7$ is —$NR_{10}R_{10}$, $R_1$ is —$OR_8$, $R_3$ is H, $R_8$ is H and each $R_9$ is H.

In an exemplary embodiment of Formula (1), $R_2$ is H, $R_7$ is —$NR_{10}R_{10}$ and at least one $R_9$ is H.

In an exemplary embodiment of Formula (1), $R_2$ is H, $R_7$ is —$NR_{10}R_{10}$ and each $R_9$ is H.

In an exemplary embodiment of Formula (1), $R_7$ is —$NR_{10}R_{10}$, each $R_{10}$ is —$CH_2CH_3$ and at least one of $R_4$ and $R_5$ is —$CH_3$.

In an exemplary embodiment of Formula (1), $R_2$ is H, $R_7$ is —$NR_{10}R_{10}$, each $R_{10}$ is —$CH_2CH_3$ and each of $R_4$ and $R_5$ is —$CH_3$.

In an exemplary embodiment of Formula (1), $R_2$ is H, $R_7$ is —$NR_{10}R_{10}$, each $R_{10}$ is —$CH_2CH_3$, $R_1$ is —$OR_8$, $R_3$ is H, each of $R_4$ and $R_5$ is —$CH_3$ and X is F, Cl, Br or I.

In an exemplary embodiment of Formula (1), $R_7$ is a heterocyclyl group selected from the group consisting of morpholinyl, pyrrolidinonyl, pyrrolidinyl, piperidinyl, piperazinyl and tetrahydropyranyl.

In an exemplary embodiment of Formula (1), $R_7$ is a heterocyclyl group selected from the group consisting of morpholinyl, piperidinyl, piperazinyl and tetrahydropyranyl.

In an exemplary embodiment of the compound of Formula (1), $R_1$ is —$OR_8$; $R_2$, $R_3$ and $R_6$ are H; $R_4$ and $R_5$ are independently $C_{1-3}$ alkyl; $R_7$ is —$NR_{10}R_{10}$ or a piperidinyl group; L is —$(CR_9R_9)_n$—; X is an organic or inorganic anion; $R_8$ is H or $C_{1-3}$ alkyl; each $R_9$ is independently H or $C_{1-3}$ alkyl; each $R_{10}$ is independently H or $C_{1-3}$ alkyl; and n is 1, 2, 3 or 4.

In a particular embodiment, X is selected from the group consisting of F, Cl, Br and I. In another particular embodiment, n is 2.

In an exemplary embodiment of the compound of Formula (1), $R_1$ is —$OR_8$; $R_2$, $R_3$, $R_6$, $R_8$ and $R_9$ are H; $R_4$ and $R_5$ are —$CH_3$; $R_7$ is a piperidinyl group; L is —$(CR_9R_9)_n$—; X is selected from the group consisting of F, Cl, Br and I; and n is 1, 2, 3 or 4.

In an exemplary embodiment of the compound of Formula (1), $R_1$ is —$OR_8$; $R_2$, $R_3$, $R_6$, $R_8$ and $R_9$ are H; $R_4$ and $R_5$ are —$CH_3$; $R_7$ is —$NR_{10}R_{10}$; each $R_{10}$ is independently $C_{1-3}$ alkyl; L is —$(CR_9R_9)_n$—; X is selected from the group consisting of F, Cl, Br and I; and n is 1, 2, 3 or 4.

In an exemplary embodiment, the compound of Formula (1) is a compound of Formula (1A):

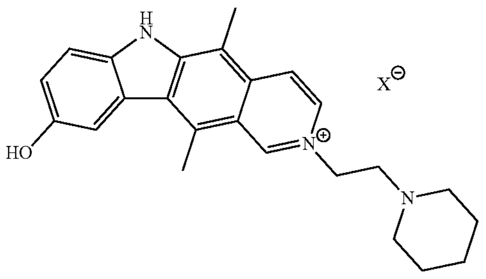

wherein X is an organic or inorganic anion. In an exemplary embodiment, X is selected from the group consisting of halo (F, Cl, Br, I), alkoxide, p-toluenesulfonate, methylsulfonate, sulfonate, phosphate, and carboxylate (such as benzoate, succinate, acetate, glycolate, maleate, malate, fumarate, citrate, tartrate, ascorbate, cinnamoate, mandeloate, and diphenylacetate). In a particular embodiment, X is selected from the group consisting of F, Cl, Br, and I.

In an exemplary embodiment, the compound of Formula (1) is Compound (1AA):

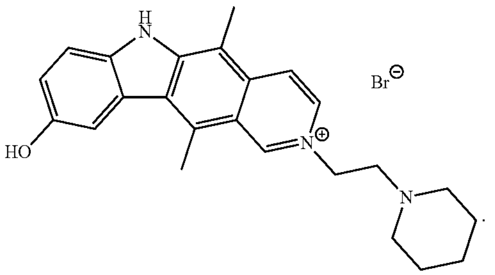 [SMILES: Cc1c2cc[n+](CCN3CCCCC3)cc2c(C)c2c1[nH]c1ccc(O)cc12 ; [Br-]]

In an exemplary embodiment, the compound of Formula (1) is a compound of Formula (1B):

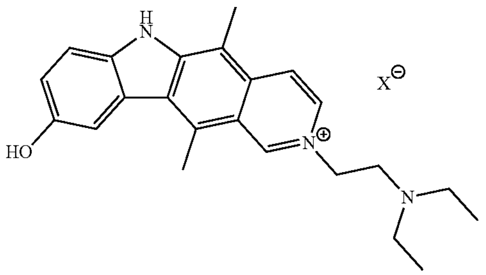

wherein X is an organic or inorganic anion. In an exemplary embodiment, X is selected from the group consisting of halo (F, Cl, Br, I), alkoxide, p-toluenesulfonate, methylsulfonate, sulfonate, phosphate, and carboxylate (such as benzoate, succinate, acetate, glycolate, maleate, malate, fumarate, citrate, tartrate, ascorbate, cinnamoate, mandeloate, and diphenylacetate). In a particular embodiment, X is selected from the group consisting of F, Cl, Br and I.

In an exemplary embodiment, the compound of Formula (1) is Compound (1BB):

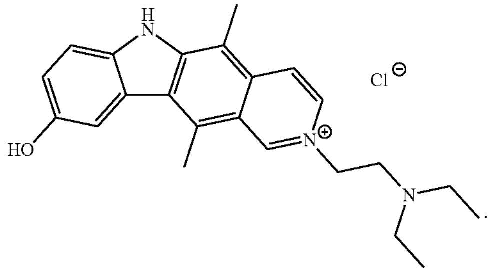 [SMILES: CCN(CC)CC[n+]1ccc2c(C)c3[nH]c4ccc(O)cc4c3c(C)c2c1 ; [Cl-]]

In an exemplary embodiment, the SETBP1 inhibitor is a compound of Formula (2):

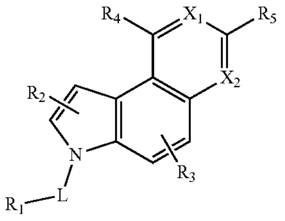

or a pharmaceutically acceptable salt thereof, wherein $R_1$ is an aryl group or a heteroaryl group, where the aryl group and the heteroaryl group each has 0 to 3 substituents independently selected from the group consisting of —$NR_6R_6$, OH, F, Cl, Br and $C_{1-3}$ alkyl;

$R_2$ and $R_3$ are independently H or $C_{1-6}$ alkyl;

$R_4$ and $R_5$ are independently H, —$NR_6R_6$ or $OR_6$;

each $R_6$ is independently H or $C_{1-3}$ alkyl;

$X_1$ and $X_2$ are independently CH or N;

L is —$(CR_7R_7)_n$—;

each $R_7$ is independently H or $C_{1-3}$ alkyl; and n is 1, 2, 3 or 4.

In an exemplary embodiment of Formula (2), the aryl or heteroaryl group of $R_1$ is selected from the group consisting of phenyl, furyl, benzofuranyl, thiophenyl, benzothiophenyl, pyrrolyl, pyridyl and pyrimidinyl.

In an exemplary embodiment of Formula (2), $R_1$ is a phenyl group having 1 substituent that is —$NR_6R_6$.

In an exemplary embodiment of Formula (2), $R_1$ is a phenyl group having 1 substituent that is —$NR_6R_6$ where at least one of $R_6$ is H.

In an exemplary embodiment of Formula (2), $R_1$ is a phenyl group having 1 substituent that is —$NR_6R_6$ where each $R_6$ is H.

In an exemplary embodiment of Formula (2), at least one of $R_2$ and $R_3$ is H.

In an exemplary embodiment of Formula (2), each of $R_2$ and $R_3$ is H.

In an exemplary embodiment of Formula (2), $X_1$ and $X_2$ are each N and at least one of $R_4$ and $R_5$ is —$NR_6R_6$.

In an exemplary embodiment of Formula (2), $X_1$ and $X_2$ are each N and each of $R_4$ and $R_5$ is —$NR_6R_6$.

In an exemplary embodiment of Formula (2), $X_1$ and $X_2$ are each N and at least one of $R_4$ and $R_5$ is —$NR_6R_6$ where each $R_6$ is H.

In an exemplary embodiment of Formula (2), $X_1$ and $X_2$ are each N and each of $R_4$ and $R_5$ is —$NR_6R_6$ where each $R_6$ is H.

In an exemplary embodiment of Formula (2), L is —$(CR_7R_7)$— and each $R_7$ is independently H or $C_{1-3}$ alkyl. In an exemplary embodiment of Formula (2), L is —$CH_2$—.

In an exemplary embodiment, the compound of Formula (2) is a compound of Formula (2A):

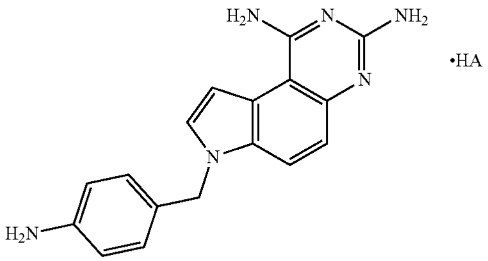 [SMILES: Nc1ccc(Cn2ccc3c4c(N)nc(N)nc4ccc32)cc1 ; "·HA"]

wherein the compound of Formula (2A) exists as a pharmaceutically acceptable salt, wherein HA is a proton donor. In an exemplary embodiment, HA is selected from the group consisting of inorganic acids (e.g., hydrochloric acid, hydrobromic acid, sulfuric acid, phosphoric acid, nitric acid, and the like) and organic acids (e.g., acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid and polygalacturonic acid). In a particular embodiment, HA is selected from the group consisting of hydrochloric acid, hydrobromic acid, sulfuric acid, phosphoric acid and nitric acid.

In an exemplary embodiment, the compound of Formula (2) is Compound (2AA):

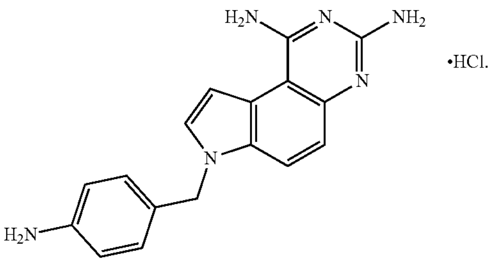 [SMILES: Nc1ccc(Cn2ccc3c4c(N)nc(N)nc4ccc32)cc1 ; "·HCl."]

Compounds as described herein may be synthesized according to methods known in the art or may be commercially available.

In an exemplary embodiment, the compound of Formula (1), Formula (1A), Compound (1AA), Formula (1B), or Compound (1BB) is present in a pharmaceutical composition comprising one or more excipients.

In an exemplary embodiment, the compound of Formula (1) is present in a pharmaceutical composition comprising one or more excipients.

In an exemplary embodiment, the compound of Formula (1A) is present in a pharmaceutical composition comprising one or more excipients.

In an exemplary embodiment. Compound (1AA) is present in a pharmaceutical composition comprising one or more excipients.

In an exemplary embodiment, the compound of Formula (1B) is present in a pharmaceutical composition comprising one or more excipients.

In an exemplary embodiment. Compound (1BB) is present in a pharmaceutical composition comprising one or more excipients.

In an exemplary embodiment, the compound of Formula (2), Formula (2A), or Compound (2AA) is present in a pharmaceutical composition comprising one or more excipients.

In an exemplary embodiment, the compound of Formula (2) is present in a pharmaceutical composition comprising one or more excipients.

In an exemplary embodiment, the compound of Formula (2A) is present in a pharmaceutical composition comprising one or more excipients.

In an exemplary embodiment. Compound (2AA) is present in a pharmaceutical composition comprising one or more excipients.

In an exemplary embodiment, a SETBP1 inhibitor and an XPO1 inhibitor are present in a pharmaceutical composition comprising one or more excipients. In an exemplary embodiment, the SETBP1 inhibitor or the XPO1 inhibitor or the combination of the SETBP1 inhibitor and the XPO1 inhibitor is present in a pharmaceutical composition comprising one or more excipients.

In an exemplary embodiment, the XPO1 inhibitor is selected from the group consisting of KPT-185, KPT-276, KPT-330, KPT-335, KPT-8602, and combination thereof. In an exemplary embodiment, the XPO1 inhibitor is selected from the group consisting of KPT-185, KPT-276, KPT-330, KPT-335 and KPT-8602.

An exemplary embodiment of the invention is a method for treating sickle cell disease (SCD) or β-thalassemia in a subject, comprising administering to the subject a therapeutically effective amount of a compound of Formula (1) (such as a compound of Formula (1A), such as Compound (1AA), such as a compound of Formula (1), such as Compound (1 TB)) or a compound of Formula (2) (such as a compound of Formula (2A), such as Compound (2AA)).

An exemplary embodiment of the invention is a method for treating sickle cell disease (SCD) or β-thalassemia in a subject, comprising administering to a subject in need thereof a therapeutically effective amount of a compound of Formula (1) (such as a compound of Formula (1A), such as Compound (1AA), or such as a compound of Formula (1B), such as Compound (1B)).

An exemplary embodiment of the invention is a method for treating sickle cell disease (SCD) or β-thalassemia in a subject, comprising administering to a subject in need thereof a therapeutically effective amount of a combination of a compound of Formula (1) (such as a compound of Formula (1A), such as Compound (1AA), or such as a compound of Formula (1B), such as Compound (1B)) and a XPO1 inhibitor.

An exemplary embodiment of the invention is a method for treating sickle cell disease (SCD) or β-thalassemia in a subject, comprising administering to a subject in need thereof a therapeutically effective amount of a combination of a compound of Formula (1) (such as a compound of Formula (1A), such as Compound (1AA), or such as a compound of Formula (1B), such as Compound (1B)) and a XPO1 inhibitor selected from the group consisting of KPT-185, KPT-276, KPT-330, KPT-335, KPT-8602 and combinations thereof.

An exemplary embodiment of the invention is a method for treating sickle cell disease or β-thalassemia in a subject, comprising administering to the subject a therapeutically effective amount of a combination of a compound of Formula (1) (such as a compound of Formula (1A), such as Compound (1AA), or such as a compound of Formula (1B), such as Compound (1BB)) or a compound of Formula (2) (such as a compound of Formula (2A), such as Compound (2AA)) and an XPO1 inhibitor selected from the group consisting of KPT-185, KPT-276, KPT-330, KPT-335, KPT-8602 and combinations thereof.

Another exemplary embodiment of the invention is a method for treating sickle cell disease or β-thalassemia in a subject, comprising administering to the subject a therapeutically effective amount of a XPO1 inhibitor selected from the group consisting of KPT-185, KPT-276, KPT-330, KPT-335, KPT-8602 and combinations thereof.

Another exemplary embodiment of the invention is a method for treating sickle cell disease (SCD) in a subject, comprising administering to a subject in need thereof a therapeutically effective amount of a XPO1 inhibitor selected from the group consisting of KPT-185, KPT-276, KPT-330, KPT-335, KPT-8602 and combinations thereof.

Another exemplary embodiment of the invention is a method for treating β-thalassemia in a subject, comprising administering to the subject a therapeutically effective amount of a SETBP1 inhibitor or a combination of a SETBP1 inhibitor and an XPO1 inhibitor. Another exemplary embodiment of the invention is a method for treating 3-thalassemia in a subject, comprising administering to the subject a therapeutically effective amount of a SETBP1 inhibitor. Another exemplary embodiment of the invention is a method for treating β-thalassemia in a subject, comprising administering to the subject a therapeutically effective amount of a combination of a SETBP1 inhibitor and an XPO1 inhibitor.

In some embodiments described herein, wherein the subject is an adult human subject or a juvenile human subject. In an exemplary embodiment, the human subject is an adult human subject. In an exemplary embodiment, the human subject is a juvenile human subject.

Some embodiments provides for a method of inducing embryonic and fetal hemoglobin expression in a cell, wherein the cell is a hematopoietic progenitor cell, an erythroid progenitor cell, or an erythroid cell, comprising contacting the cell with a SETBP1 inhibitor, an XPO1 inhibitor, or a combination of a SETBP1 inhibitor and an XPO1 inhibitor.

In an exemplary embodiment, the invention provides a pharmaceutical composition comprising at least one pharmaceutically acceptable carrier, in addition to one or more of the compounds described herein. The composition can be present in any suitable form for the desired route of administration. Where the composition is to be administered orally, any suitable orally deliverable dosage form can be used, including, without limitation, tablets, capsules (solid or liquid filled), powders, granules, syrups and other liquids, elixirs, inhalants, troches, lozenges and solutions. Injectable compositions or i.v. infusions are also provided in the form of solutions, suspensions, and emulsions.

The compounds of the invention can be formulated as described herein and are suitable for administration in a therapeutically effective amount to the subject in any number of ways. A therapeutically effective amount of a compound as described herein depends upon the amounts and types of excipients employed, the amounts and specific types of active ingredients present in a dosage form, and the route by which the compound is to be administered to patients.

Typical dosage levels for the compounds of the invention generally range from about 0.001 to about 100 mg per kg of the subject's body weight per day which can be administered in single or multiple doses. An exemplary dosage is about 0.01 to about 25 mg/kg per day or about 0.05 to about 10 mg/kg per day. In other exemplary embodiments, the dosage level ranges from about 0.01 to about 25 mg/kg per day, such as about 0.05 to about 10 mg/kg per day, or about 0.1 to about 5 mg/kg per day.

A dose can typically range from about 0.1 mg to about 2000 mg per day and can be given as a single once-a-day dose or, alternatively, as divided doses throughout the day, optionally taken with food. In a particular embodiment, the daily dose is administered twice daily in equally divided doses. A daily dose range can range from about 5 mg to about 500 mg per day such as, for example, between about 10 mg and about 300 mg per day. In managing the patient, the therapy can be initiated at a lower dose, such as from about 1 mg to about 25 mg, and increased if necessary up to from about 200 mg to about 2000 mg per day as either a single dose or divided doses, depending on the subject's global response.

Suitable oral compositions in accordance with the invention include, without limitation, tablets, troches, lozenges, aqueous or oily suspensions, dispersible powders or granules, emulsion, hard or soft capsules, syrups or elixirs. Inventive compositions suitable for oral use may be prepared according to any method known to the art for the manufacture of pharmaceutical compositions. For example, liquid formulations of the compounds can contain one or more agents selected from the group consisting of sweetening agents, flavoring agents, coloring agents and preserving agents in order to provide pharmaceutically elegant and palatable preparations of the active agents.

For tablet compositions, typical non-toxic pharmaceutically acceptable excipients include, without limitation, inert diluents such as calcium carbonate, sodium carbonate, lactose, calcium phosphate or sodium phosphate; granulating and disintegrating agents such as, for example, corn starch, or alginic acid; binding agents such as, for example, starch, gelatin or lubricating agents such as, for example, magnesium stearate, stearic acid or talc. The tablets may be uncoated or, alternatively, they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent such as, for example, calcium carbonate, calcium phosphate or kaolin, or as soft gelatin capsules wherein the active ingredient is mixed with water or an oil medium such as, for example peanut oil, liquid paraffin or olive oil.

For aqueous suspensions, the compound is admixed with excipients suitable for maintaining a stable suspension. Examples of such excipients include, without limitation, sodium carboxymethylcellulose, methylcellulose, hydropropylmethylcellulose, sodium alginate, polyvinylpyrrolidone, gum tragacanth and gum acacia.

Oral suspensions can also contain dispersing or wetting agents, such as naturally-occurring phosphatide such as, for example, lecithin, or condensation products of an alkylene oxide with fatty acids such as, for example, polyoxyethylene stearate, or condensation products of ethylene oxide with long chain aliphatic alcohols such as, for example, heptadecaethyleneoxycetanol, or condensation products of ethylene oxide with partial esters derived from fatty acids and a hexitol such as, for example, polyoxyethylene sorbitol monooleate, or condensation products of ethylene oxide with partial esters derived from fatty acids and hexitol anhydrides such as, for example, polyethylene sorbitan monooleate. The aqueous suspensions may also contain one or more preservatives such as, for example, ethyl or n-propyl p-hydroxybenzoate, one or more coloring agents, one or more flavoring agents, and one or more sweetening agents such as sucrose or saccharin.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water can provide the active ingredient in admixture with a dispersing or wetting agent, suspending agent and one or more preservatives. Suitable dispersing or wetting agents and suspending agents are exemplified by those already mentioned above. Additional excipients such as, for example, sweetening, flavoring and coloring agents, may also be present.

Syrups and elixirs may be formulated with sweetening agents such as, for example, glycerol, propylene glycol, sorbitol or sucrose. Such formulations may also contain a demulcent, a preservative, and flavoring and coloring agents.

Compositions for parenteral administrations are formulated in a sterile medium suitable for intravenous, intramuscular or intrathecal delivery. A sterile injectable preparation of the compounds may be in the form of a sterile injectable solution or sterile injectable suspension. Non-toxic, parentally acceptable diluents or solvents such as, for example, 1,3-butanediol can be used to formulate the parenteral compositions. Among the acceptable vehicles and solvents that may be employed are water, Ringer's solution and isotonic sodium chloride solution. In addition, sterile oils also can be employed as a solvent or a suspending medium. For this purpose, any bland fixed oil may be employed, including synthetic monoglycerides or diglycerides. In addition, fatty acids such as oleic acid can be used in the preparation of injectables.

Depending on the vehicle used and the concentration of the drug in the formulation, the parenteral formulation can contain other adjuvants such as local anesthetics, preservatives and buffering agents.

In addition to using shRNA technology, siRNA technology, antibodies, or small molecule inhibitors of SETBP1 or XPO1, it is reasonable for a person of skilled in the art to use gene editing technologies to inhibit the expression levels of SETBP1 or XPO1 and as a result to enhance the expression levels of embryonic and fetal hemoglobins. The editing, for instance, can introduce a mutation to the active site, a premature stop codon or a frameshift mutation into the SETBP1 or XPO1 gene. Gene editing technologies may include, but are not limited to, a CRISPR/Cas9 system, a CRISPR/Cas13 system, a zinc finger nuclease system, a TALEN system, and a meganuclease system. These gene editing technologies themselves are described in public domain (e.g. U.S. Pat. No. 10,196,652, Science: Vol. 358, Issue 6366, pp. 1019-1027. DOI: 10.1126/science.aaq0180).

In some embodiments, the SETBP1 inhibitor is one or more components of a gene editing system targeting one or more sites within a gene encoding SETBP1 or a regulatory element thereof, a nucleic acid molecule encoding the one or more components of the gene editing system, or a combination thereof. In some embodiments, the SETBP1 inhibitor is a gene editing system, and wherein the gene editing system is selected from the group consisting of CRISPR/Cas9, CRISPR/Cas13, a zinc finger nuclease system, a TALEN system, and a meganuclease system. In some embodiments, the gene editing system is a CRISPR/Cas9 system. In some embodiments, the gene editing system is a CRISPR/Cas13 system. In some embodiments, the gene editing system is a zinc finger nuclease system. In some embodiments, the gene editing system is a TALEN system. In some embodiments, the gene editing system is a meganuclease system. In some embodiments, the SETBP1 inhibitor comprises a guide RNA molecule comprising a tracr and a crRNA. In some embodiments, the crRNA comprises a targeting domain that is complementary with a target sequence of SETBP1.

In some embodiments, the XPO1 inhibitor is one or more components of a gene editing system targeting one or more sites within a gene encoding XPO1 or a regulatory element thereof, a nucleic acid molecule encoding the one or more components of the gene editing system, or a combination thereof. In some embodiments, the XPO1 inhibitor is a gene editing system, and wherein the gene editing system is selected from the group consisting of CRISPR/Cas9, CRISPR/Cas13, a zinc finger nuclease system, a TALEN system, and a meganuclease system. In some embodiments, the gene editing system is a CRISPR/Cas9 system. In some embodiments, the gene editing system is a CRISPR/Cas13 system. In some embodiments, the gene editing system is a zinc finger nuclease system. In some embodiments, the gene editing system is a TALEN system. In some embodiments, the gene editing system is a meganuclease system. In some embodiments, the XPO1 inhibitor comprises a guide RNA molecule comprising a tracr and a crRNA. In some embodiments, the crRNA comprises a targeting domain that is complementary with a target sequence of XPO1.

The pharmaceutical compositions according to the invention may contain one or more additional therapeutic agents, for example, to increase efficacy and/or to decrease side effects. Examples of such agents include, without limitation, agents to treat or inhibit immunological, inflammatory, autoimmune or allergic disorders.

EXAMPLES

Protocol

For studies using MEL cells, the cells were treated with selected inhibitors or vehicle in a culture medium (RPM 11640 medium with 10% fetal bovine serum) for 48 hours and were subsequently harvested for analysis of relative mRNA levels of Hbb-bh1, Hbb-y, and Hbb-b1 using real-time RT-PCR. For studies using primary human CD34+ hematopoietic stem and progenitor cells, the cells were treated with inhibitors or vehicle following or concurrent with induction of erythroid differentiation using an established two-phase culture protocol (Xu et al., Genes & Development 24(8): 783-798 (2010)). Relative mRNA levels of β-like globin genes in human cells after treatment were also analyzed using real-time RT-PCR.

The non-targeting control pLKO.1 lentiviral shRNA construct shNC was purchased from Sigma (SHC002). Lentiviral shRNA constructs targeting Setbp1 (sh84 and sh8) were generated by cloning Setbp1 targeting sequences (sh84, CGG CTT TGA ATC CCA ATC ATT (SEQ ID NO:1); sh8, CCT ATG ATG AAC CTT GGT TAT (SEQ ID NO:2)) into pLKO.1. To generate infectious lentivirus, the constructs were co-transfected using FuGENE 6 transfection reagent into 293T cells along with packaging plasmid A8.9 and a plasmid expressing VSV-G, and virus were harvested at 72 hours after transfection. Viral titers were calculated by infecting NIH-3T3 cells with serial dilutions of viral stocks and counting puromycin resistant colonies. Lentiviral infections were performed by spinoculation in which a mixture of lentivirus and MEL cells at 4:1 ratio in 24-well plates were spun at 2000×g for 90 minutes at 37° C. Puromycin (2 μg/mL) was added to culture at 24 hours after spinoculation to select for infected cells.

Results

To evaluate whether Setbp1 plays a role in the repression of embryonic and fetal hemoglobin expression, the expression levels of Setbp1 were knocked down using two different lentiviral shRNAs in MEL cells, which is a mouse erythroid progenitor cell line conventionally used for studying repression of embryonic and fetal hemoglobins. Unexpectedly, the Setbp1 knockdowns significantly increased the mRNA levels of embryonic (Hbb-bh1) and fetal (Hbb-y) hemoglobin genes (FIG. 1), suggesting that Setbp1 is a repressor of their transcription.

Figure 2:
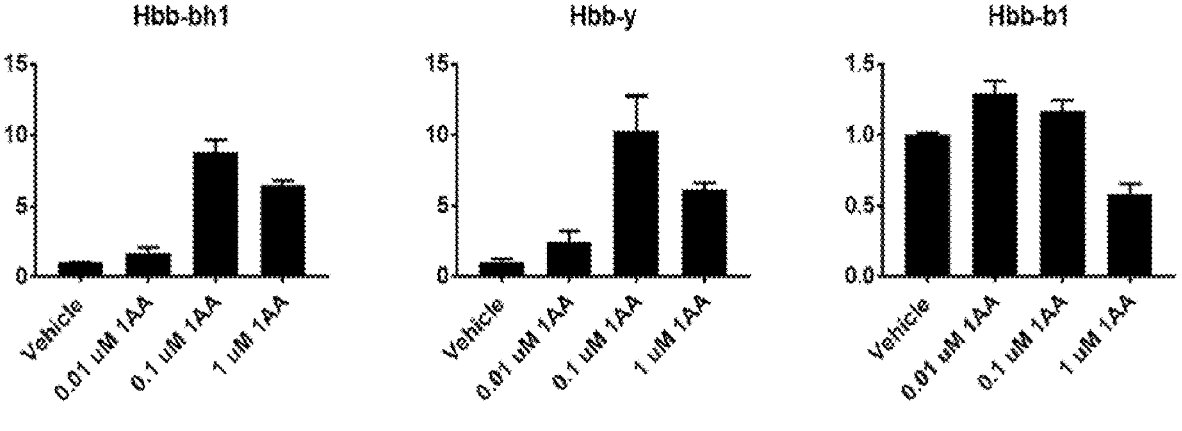
FIG. 2 shows that Compound (1AA) increased embryonic and fetal hemoglobin expression levels in MEL cells. Real-time RT-PCR analysis of Hbb-bh1, Hbb-y, and Hbb-b1 mRNA levels in MEL cells after 48 hours of treatment with compound 1AA at indicated concentration or with control DMSO. Relative expression levels were calculated by normalizing to Rpl4 mRNA levels in the same sample and also to cells infected with DMSO.
Figure 6:
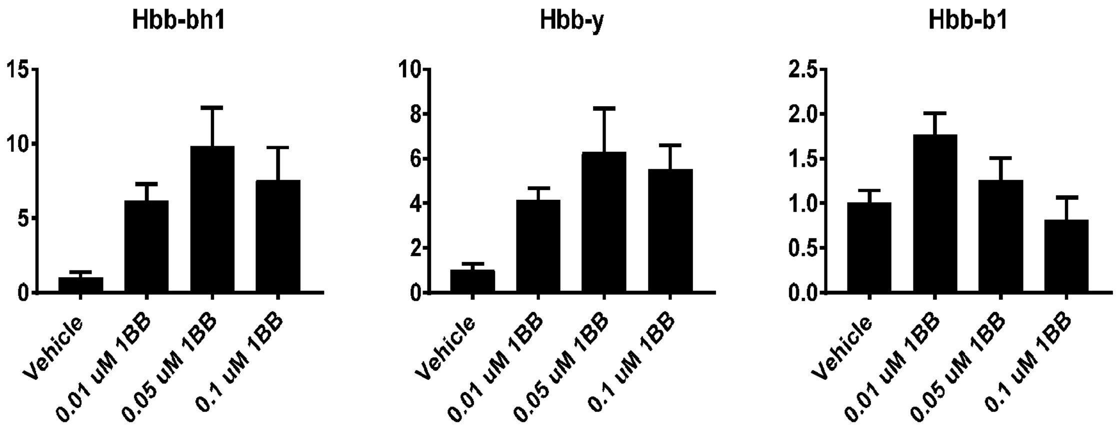
FIG. 6 shows that Compound (1BB) increased embryonic and fetal hemoglobin expression levels in MEL cells. Real-time RT-PCR analysis of Hbb-bh1, Hbb-y and Hbb-b1 mRNA levels in MEL cells after 48 hours of treatment with compound (1BB) at indicated concentration or with vehicle water. Relative expression levels were calculated by normalizing to Rpl4 mRNA levels in the same sample and also to cells treated with water.

Compound (1AA), which has been identified as an inhibitor of SETBP1 transcriptional activity (WO2019/226773), was tested for its effect on the expression of Hbb-bh1 and Hbb-y in MEL cells. Consistent with Setbp1 knockdown studies, treatment with Compound (1AA) at 0.1 μM for 48 hours led to over an 8-fold increase in the mRNA levels of both Hbb-bh1 and Hbb-y (FIG. 2). This unexpectedly potent activating effect of Compound (1AA) appears limited to embryonic and fetal hemoglobin since only minor changes in the levels of adult hemoglobin Hbb-b1 were detected under the same conditions (FIG. 2). Similarly, Compound (1BB), another inhibitor of SETBP1 (WO2019/226773), was also observed to significantly increase the expression of Hbb-bh1 and Hbb-y in MEL cells while having minor effects on Hbb-b1 mRNA levels (FIG. 6).

Figure 3:
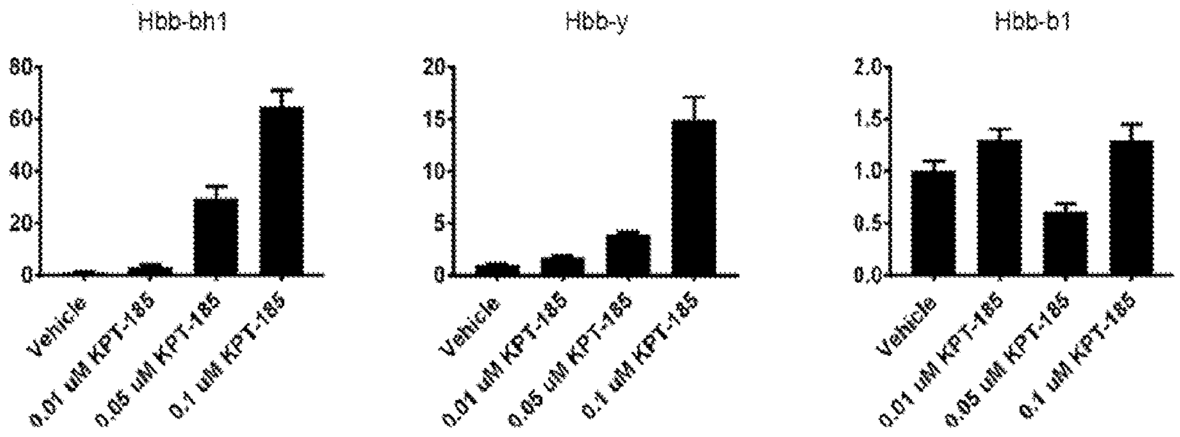
FIG. 3 shows that the XPO1 inhibitor KPT-185 increased embryonic and fetal hemoglobin expression levels in MEL cells. Real-time RT-PCR analysis of Hbb-bh1, Hbb-y, and Hbb-b1 mRNA levels in MEL cells after 48 hours of treatment with KPT-185 (KPT) at indicated concentration or with control DMSO. Relative expression levels were calculated by normalizing to Rpl4 mRNA levels in the same sample and also to cells infected with DMSO.
Figure 7:
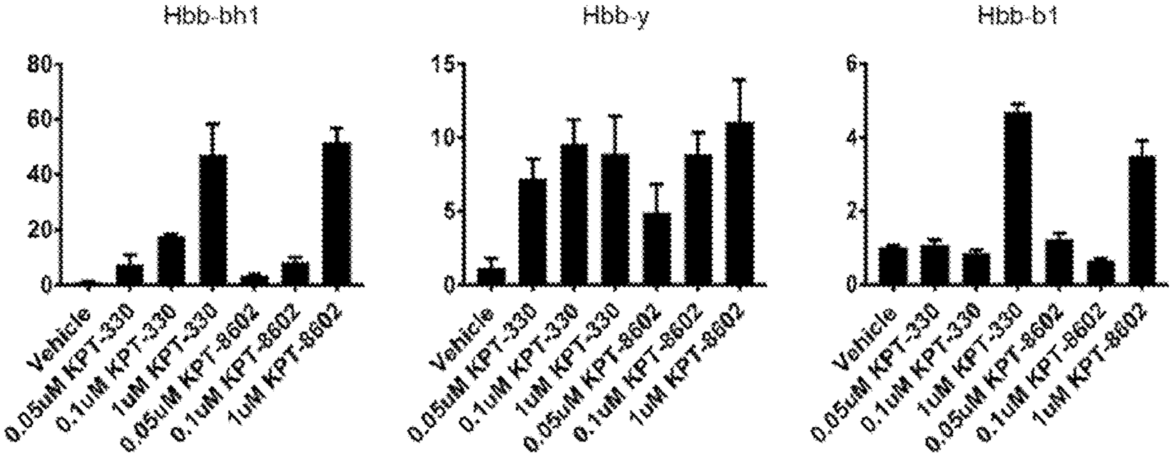
FIG. 7 shows KPT-330 and KPT-8602 increased embryonic and fetal hemoglobin expression levels in MEL cells. Real-time RT-PCR analysis of Hbb-bh1, Hbb-y and Hbb-b1 mRNA levels in MEL cells after 48 hours of treatment with KPT-330 and KPT-8602 at indicated concentration or with vehicle DMSO. Relative expression levels were calculated by normalizing to Rpl4 mRNA levels in the same sample and also to cells treated with DMSO.

Compound (1AA) has been shown to inhibit the activity of SETBP1 by blocking its interaction with key cofactor XPO1 (WO2019/226773). This interaction between SETBP1 and XPO1 can also be blocked by XPO1 inhibitors such as, but not limited to, KPT-185 and KPT-330. Therefore, XPO1 inhibitors were also tested for their effect on the expression of Hbb-bh1 and Hbb-y in MEL cells. Treatment with 0.1 μm KPT-185 for 48 hours was observed to increase mRNA levels of Hbb-bh1 and Hbb-y by over 60-fold and over 14-fold, respectively (FIG. 3). Similarly, two other XPO1 inhibitors KPT-330 and KPT-8602 also were found to significantly increase mRNA levels of Hbb-bh1 and Hbb-y in MEL cells (FIG. 7). These results clearly show that XPO1 inhibitors are also surprisingly efficient in activating embryonic and fetal hemoglobin expression. Similar to Compounds (1AA) and (1BB), XPO1 inhibitors also a exerted minimal effect on the expression levels of Hbb-b1 (FIG. 2 and FIG. 7).

Figure 4:
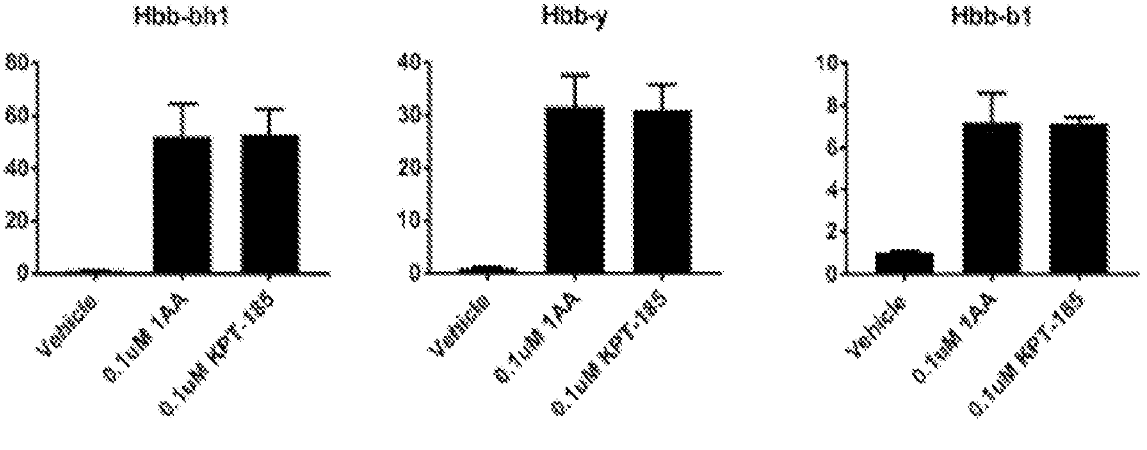
FIG. 4 shows the long-lasting effects of Compound (1AA) and KPT-185. Real-time RT-PCR analysis of Hbb-bh1, Hbb-y, and Hbb-b1 mRNA levels in MEL cells 48 hours after removal of Compound (1AA) or KPT-185 from culture. The cells were first treated with Compound (1AA) or KPT-185 for 24 hours. Relative expression levels were calculated by normalizing to Rpl4 mRNA levels in the same sample and also to cells treated with DMSO.

A further experiment examined whether continuous treatment of Compound (1AA) and KPT-185 as exemplary SETBP1 and XPO1 inhibitors, respectively, was required for activation of Hbb-bh1 and Hbb-y expression. MEL cells were treated with Compound (1AA) and KPT-185 for 24 hours and the Hbb-bh1 and Hbb-y mRNA levels were then examined at 48 hours after their removal. Significantly elevated levels of Hbb-bh1 and Hbb-y mRNA were still detected in MEL cells (FIG. 4). These results show a long-lasting activation effect of Compound (1AA) and KPT-185 on Hbb-bh1 and Hbb-y expression.

Figure 5:
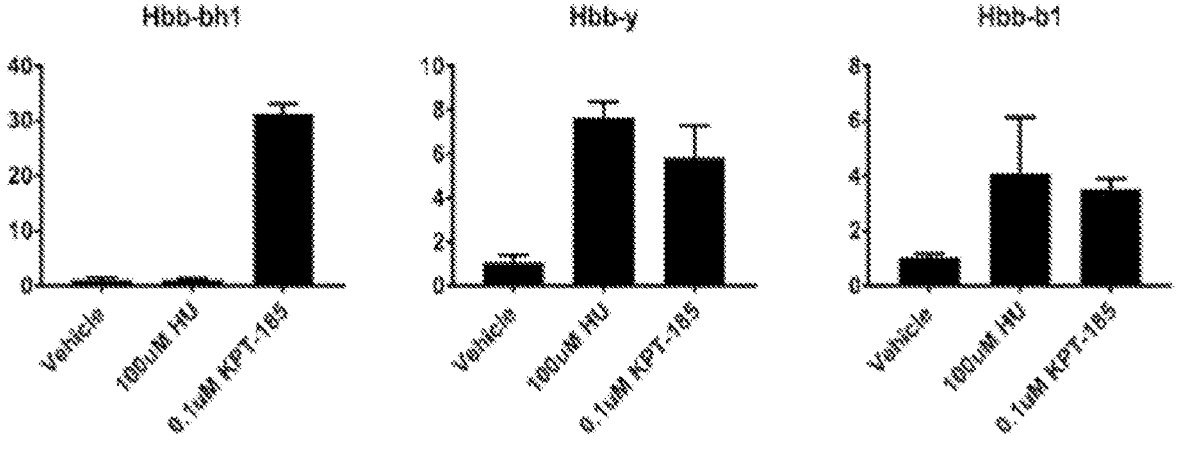
FIG. 5 shows that KPT-185 is more effective than hydroxyurea in increasing embryonic hemoglobin expression in MEL cells. Real-time RT-PCR analysis of Hbb-bh1, Hbb-y, and Hbb-b1 mRNA levels in MEL cells after 48 hours of treatment with hydroxyurea (HU), KPT-185 (KPT), or control DMSO. Relative expression levels were calculated by normalizing to Rpl4 mRNA levels in the same sample and also to cells treated with DMSO.

The ability of KPT-185 to activate Hbb-bh1 and Hbb-y expression in MEL cells was also compared to that of hydroxyurea, an FDA-approved drug for sickle cell disease. While KPT-185 was observed to activate Hbb-y expression to similar levels to that of hydroxyurea, surprisingly KPT-185 was substantially more effective than hydroxyurea in activating Hbb-bh1 expression with almost 30-fold higher levels of Hbb-bh1 mRNA being detected in cells treated with KPT-185 compared to cells treated with hydroxyurea (FIG. 5). This finding shows that XPO1 inhibitors such as KPT-185 are more effective than hydroxyurea in treating sickle cell disease.

Erythroid Differentiation and Treatment of Human $CD34^+$ Cells

Figure 8:
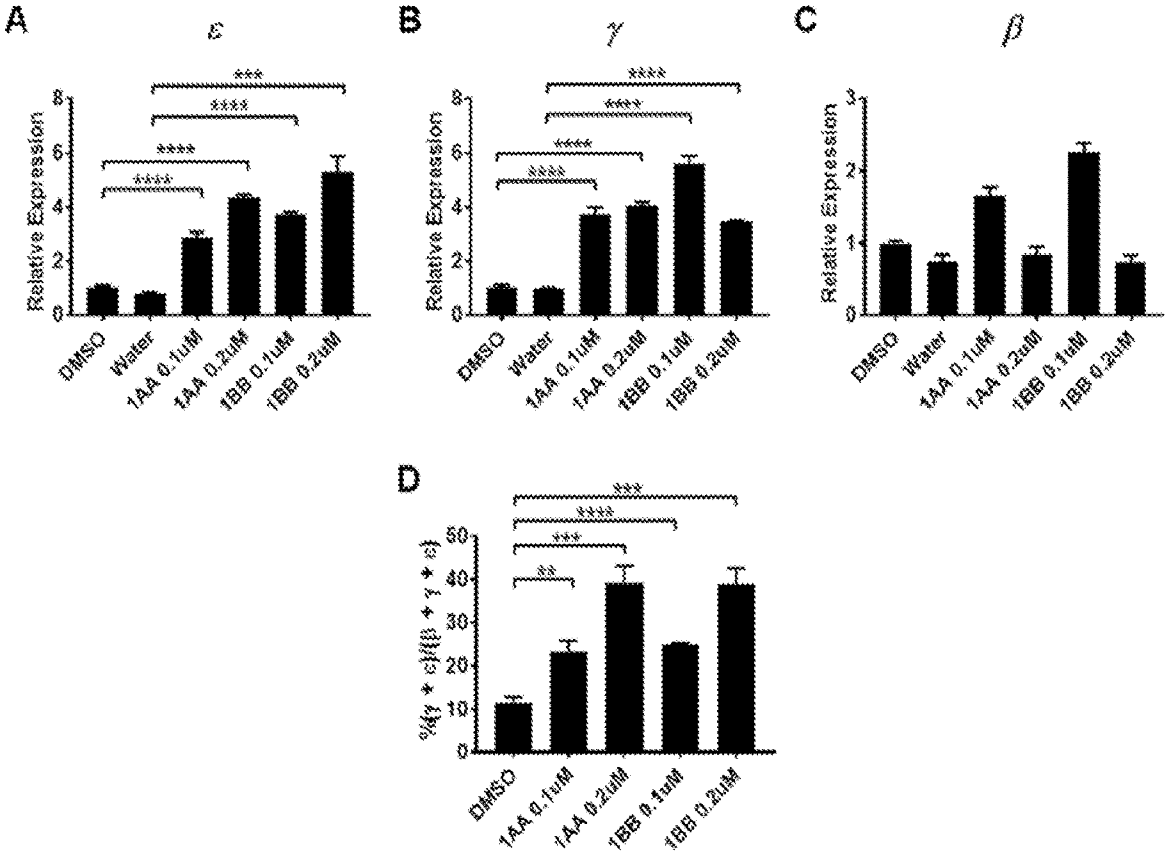
FIG. 8 shows that Compound 1AA and 1BB significantly increased embryonic and fetal hemoglobin expression levels in human erythroid cells. Human $CD34^+$ cells mobilized by granulocyte-colony stimulating factor (G-CSF) were induced to undergo erythroid differentiation in culture. Treatment with Compound 1AA and 1BB at indicated concentrations or vehicles (DMSO or water) were started at day 5 of expansion condition. Erythroid cells were harvested at day 10 of differentiation condition for real-time RT-PCR analysis of human embryonic s (FIG. 8A), fetal γ (FIG. 8B), and adult β (FIG. 8C) hemoglobin mRNA levels. Relative expression levels were calculated by normalizing to RPL4 mRNA levels in the same sample and also to cells treated with DMSO.

Primary human mobilized $CD34^+$ cells were initially cultured in expansion medium containing StemSpan SFEM Medium (StemCell Technologies Inc.) with 1×CC100 cytokine mix (StemCell Technologies Inc.) and 2% Penicillin-Streptomycin (Life Technologies Inc.). Cells were maintained in this expansion medium at a density of $0.1\text{-}1\times10^6$ cells/mL for a total of six days with media changes every two days. On day 6, cells were transferred into differentiation medium containing StemSpan SFEM Medium with 2% Penicillin-Streptomycin, 20 ng/ml SCF (Biolegend), 1 U/ml EPO (Amgen), 5 ng/ml IL-3 (Biolegend), 2 μM dexamethasone (Sigma), and 1 μM β-estradiol (Sigma). Cells were maintained at a density of $0.1\text{-}1\times10^6$ cells/mL in differentiation medium for 10 days with media changes every two days. Drug treatments were started at day 5 of expansion condition and maintained thereafter. Fresh drugs were added at each medium change. The data is summarized in FIG. 8.

All patents and publications cited herein are incorporated by reference in their entireties.

What is claimed is:

1. A method of inducing embryonic or fetal hemoglobin expression in a subject in need thereof, comprising administering to the subject a therapeutically effective amount of a SETBP1 inhibitor, wherein the SETBP1 inhibitor is a compound of Formula (1A) or Formula (1B):

(1A)

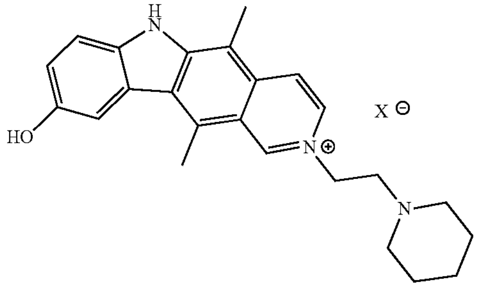

(1B)

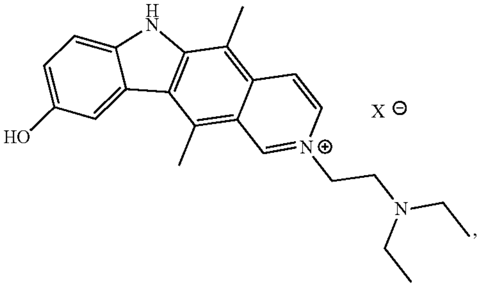

wherein X is selected from the group consisting of F, Cl, Br, and I, wherein the subject is identified with a condition treatable by expression of embryonic and fetal hemoglobin.

2. The method of claim 1, wherein the SETBP1 inhibitor is a compound of Formula (1A):

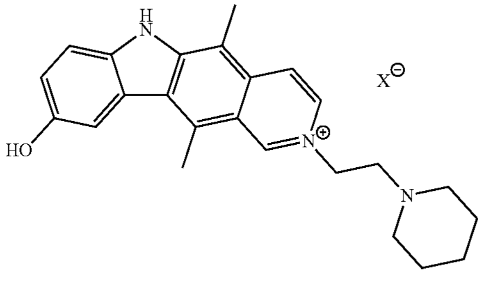

wherein X is selected from the group consisting of F, Cl, Br, and I.

3. The method of claim 1, wherein the SETBP1 inhibitor is Compound (1AA)

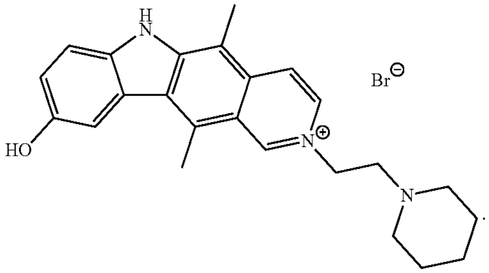 [SMILES: Cc1c2cc[n+](CCN3CCCCC3)cc2c(C)c2c1[nH]c1ccc(O)cc12 ; [Br-]]

4. The method of claim 1, wherein the SETBP1 inhibitor is a compound of Formula (1B):

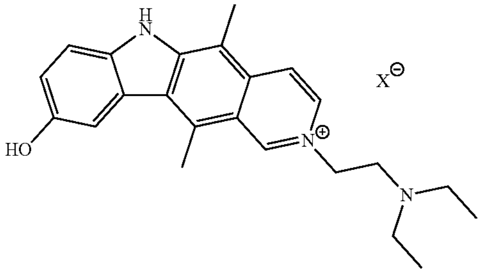

wherein X is selected from the group consisting of F, Cl, Br, and I.

5. The method of claim 1, wherein the SETBP1 inhibitor is Compound (1BB):

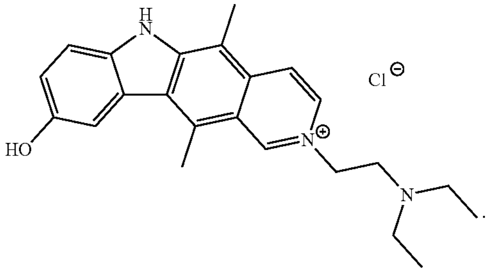 [SMILES: CCN(CC)CC[n+]1ccc2c(C)c3[nH]c4ccc(O)cc4c3c(C)c2c1 ; [Cl-]]

6. The method of claim 1, wherein the condition is sickle cell disease (SCD) or β-thalassemia.

7. The method of claim 1, further comprising administering a XPO1 inhibitor selected from the group consisting of KPT-185, KPT-276, KPT-330, KPT-335, and KPT-8602.

* * * * *